US00PP37088P2

(12) United States Plant Patent
Bernuetz

(10) Patent No.: US PP37,088 P2
(45) Date of Patent: Nov. 4, 2025

(54) ***EUPHORBIA* PLANT NAMED 'BONPRI 16P5'**

(50) Latin Name: ***Euphorbia pulcherrima* Willd. ex Klotzsch X *Euphorbia cornastra***
Varietal Denomination: BONPRI 16P5

(71) Applicant: Andrew Bernuetz, Yellow Rock (AU)

(72) Inventor: Andrew Bernuetz, Yellow Rock (AU)

(73) Assignee: BONZA BOTANICALS PTY, LTD., Yellow Rock (AU)

( * ) Notice: Subject to any disclaimer, the term of this patent is extended or adjusted under 35 U.S.C. 154(b) by 0 days.

(21) Appl. No.: 19/183,823

(22) Filed: Apr. 19, 2025

(51) Int. Cl.
*A01H 6/38* (2018.01)
*A01H 5/02* (2018.01)

(52) U.S. Cl.
USPC ..... Plt./306

(58) Field of Classification Search
USPC ..... Plt./306
CPC ..... A01H 6/385; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Euphorbia* plant named 'BONPRI 16P5', characterized by its relatively compact, upright and mounded plant habit; vigorous growth habit; freely branching habit; relatively early flowering habit; inflorescences with purplish pink-colored flower bracts with lighter purplish pink-colored marginal edges; inflorescences with tight cyathia clusters; and good post-production longevity.

2 Drawing Sheets

Figure 1:
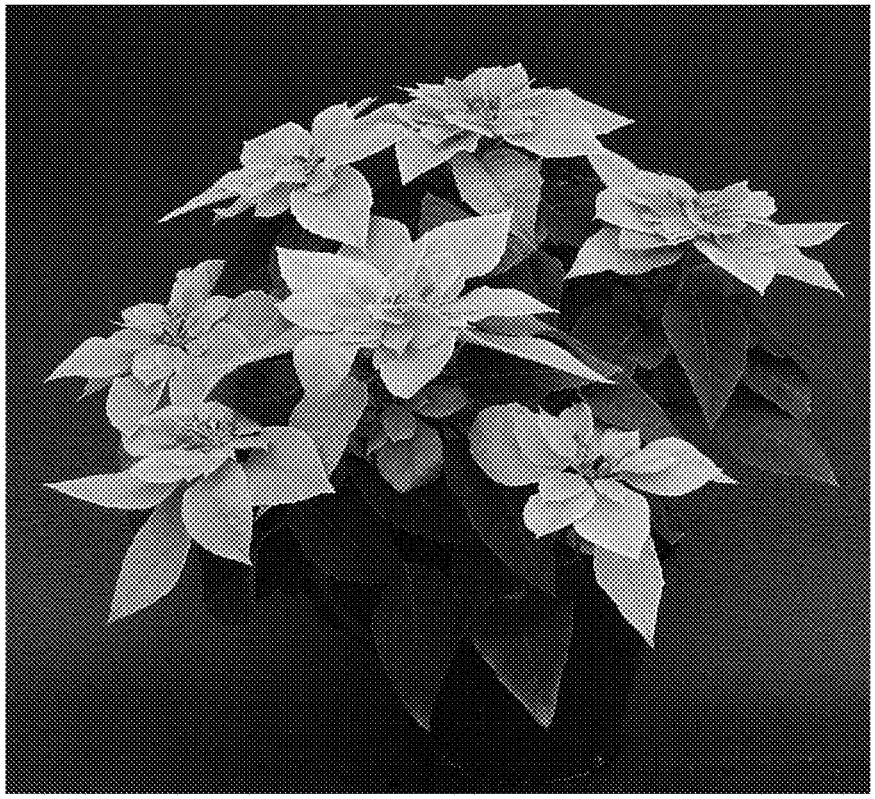

Botanical designation: *Euphorbia pulcherrima* Willd. ex Klotzsch X *Euphorbia cornastra.*

Cultivar denomination: 'BONPRI 16P5'.

CROSS-REFERENCED TO CLOSELY-RELATED APPLICATIONS

A Japanese Plant Breeder's Rights application for the instant plant was filed by the Inventor/Applicant and Assignee on Mar. 26, 2018, application number 32967. Foreign priority is not claimed to this application.

BACKGROUND OF THE INVENTION

The present invention relates to a new and distinct cultivar of *Euphorbia* plant, an interspecific hybrid botanically known as *Euphorbia pulcherrima* Willd. ex Klotzsch X *Euphorbia cornastra*, and hereinafter referred to by the cultivar name 'BONPRI 16P5'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit that flower relatively early and have attractive flower bracts.

The new *Euphorbia* plant is a naturally-occurring whole plant mutation of *Euphorbia pulcherrima* Willd. ex Klotzsch X *Euphorbia cornastra* 'BONPRI 9276', disclosed in U.S. Plant Pat. No. 27,721. The new *Euphorbia* plant was discovered and selected by the Inventor as a single flowering plant from within a population of plants of the mutation parent selection in a controlled greenhouse environment in Yellow Rock, New South Wales, Australia on Dec. 3, 2016.

Asexual reproduction of the new *Euphorbia* plant by terminal vegetative cuttings in a controlled greenhouse environment in Yellow Rock, New South Wales, Australia since December 2016 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'BONPRI 16P5'. These characteristics in combination distinguish 'BONPRI 16P5' as a new and distinct *Euphorbia* plant:

1. Relatively compact, upright and mounded plant habit.
2. Vigorous growth habit.
3. Freely branching habit.
4. Relatively early flowering habit.
5. Inflorescences with purplish pink-colored flower bracts with lighter purplish pink-colored marginal edges.
6. Inflorescences with tight cyathia clusters.
7. Good post-production longevity.

Plants of the new *Euphorbia* differ primarily from plants of the mutation parent, 'BONPRI 9276', in time to flower as plants of the new *Euphorbia* flower about three days earlier than plants of 'BONPRI 9276'. In addition, flower bracts of plants of the new *Euphorbia* have shorter petioles than flower bracts of plants of 'BONPRI 9276'.

Plants of the new *Euphorbia* can be compared to plants of the *Euphorbia pulcherrima* Willd. ex Klotzsch X *Euphorbia cornastra* 'Bonpripicom', disclosed in U.S. Plant Pat. No. 21,325. In side-by-side comparisons, plants of the new *Euphorbia* differ primarily from plants of 'Bonpripicom' in the following characteristics:

1. Plants of the new *Euphorbia* are not as compact as plants of 'Bonpripicom'.

2. Plants of the new *Euphorbia* are more freely branching and freely flowering than plants of 'Bonpripicom'.
3. Plants of the new *Euphorbia* flower about three days earlier than plants of 'Bonpripicom'.
4. Plants of the new *Euphorbia* have more flower bracts per inflorescence than plants of 'Bonpripicom'.
5. Flower bracts of plants of the new *Euphorbia* are elliptic in shape whereas flower bracts of plants of 'Bonpripicom' are ovate in shape.
6. Flower bracts of plants of the new *Euphorbia* have shorter petioles than flower bracts of plants of 'Bonpripicom'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph on the first sheet (FIG. 1) is a side perspective view of a typical flowering plant of 'BONPRI 16P5' grown in a container.

Figure 2:
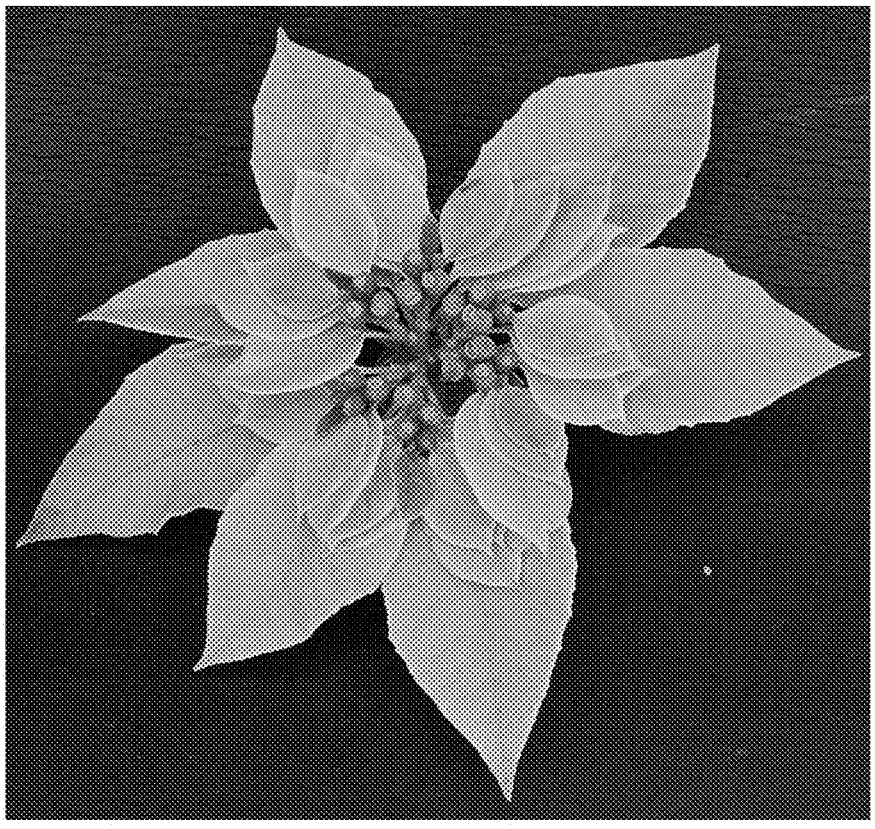

The photograph on the second sheet (FIG. 2) is a close-up view of a typical inflorescence of 'BONPRI 16P5'.

DETAILED BOTANICAL DESCRIPTION

Plants used in the aforementioned photographs and described herewith in detail were grown during the autumn and early winter in 10.5-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. ex Klotzsch X *Euphorbia cornastra* 'BONPRI 16P5'.

Parentage: Naturally-occurring whole plant mutation of *Euphorbia pulcherrima* Willd. ex Klotzsch X *Euphorbia cornastra* 'BONPRI 9276', disclosed in U.S. Plant Pat. No. 27,721.

Propagation:

*Type*.—Terminal vegetative cuttings.

*Time to initiate roots, summer*.—About ten days at temperatures about 20° C. to 21° C.

*Time to initiate roots, winter*.—About twelve days at temperatures about 20° C. to 21° C.

*Time to produce a rooted young plant, summer*.—About 24 days at temperatures about 20° C. to 21° C.

*Time to produce a rooted young plant, winter*.—About 28 days at temperatures about 20° C. to 21° C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Relatively compact, upright and mounded plant habit; inverted triangle; inflorescences positioned above the foliar plane; vigorous growth habit.

*Plant height*.—About 23.2 cm.

*Plant diameter or spread*.—About 36.4 cm.

*Lateral branch description*.—Branching habit: Freely branching habit, about eight lateral branches develop per plant. Length: About 16.6 cm. Diameter: About 3.7 mm. Internode length: About 2.3 cm. Aspect: Mostly upright to outwardly. Strength: Moderately strong. Texture and luster: Sparsely pubescent; glossy. Color: Close to 146A.

*Leaf description*.—Arrangement: Alternate, simple. Length: About 8.2 cm. Width: About 4.7 cm. Shape: Ovate. Apex: Acute. Base: Rounded. Margin: Mostly entire or shallowly serrate; slightly undulate. Venation pattern: Pinnate, reticulate. Texture and luster, upper and lower surfaces: Sparsely pubescent; matte. Color: Developing leaves, upper surface: Close to between 143A and 144A. Developing leaves, lower surface: Close to 144A. Fully developed leaves, upper surface: Close to between NN137A and 139A; venation, close to 144C. Fully developed leaves, lower surface: Close to NN137C; venation, close to 144D. Petioles: Length: About 2.4 cm. Diameter: About 2.3 mm. Texture, upper and lower surfaces: Sparsely pubescent. Color, upper surface: Close to 146B moderately tinted with close to N199A. Color, lower surface: Close to 146B.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about eight inflorescences develop per plant.

*Inflorescence diameter*.—About 15.4 cm.

*Inflorescence height*.—About 3.7 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering response, plants flower about 49 to 50 days under natural season or photoinductive conditions in Japan.

*Post-production longevity*.—Good post-production longevity; plants of the new *Euphorbia* maintain good substance and bract color for about six to eight weeks.

*Flower bracts*.—Quantity per inflorescence: About 27. Length, largest bracts: About 3.4 cm. Width, largest bracts: About 1.9 cm. Aspect: Mostly horizontal and flat. Shape: Elliptic. Apex: Cuspidate. Base: Obtuse. Margin: Entire. Texture and luster, upper and lower surfaces: Smooth, glabrous; matte. Venation pattern: Pinnate, reticulate. Color: Transitional bracts, upper surface: Random sectors, close to NN137B and 55B. Transitional bracts, lower surface: Random sectors, close to 138B and 158C. Developing bracts, upper surface: Close to N57A. Developing bracts, lower surface: Close to 58D. Fully expanded bracts, upper surface: Close to N57D; along midvein, closer to N57C; narrow marginal edges, close to 62D; venation, close to 60D; flower bracts resist fading with subsequent development. Fully expanded bracts, lower surface: Close to 62C; narrow marginal edges, close to 62D; venation, close to 145B; flower bracts resist fading with subsequent development. Flower bract petioles: Length: About 6.8 mm. Diameter: About 1.5 mm. Texture, upper and lower surfaces: Sparsely pubescent. Color, upper surface: Close to 145C tinted with close to 63C. Color, lower surface: Close to 145B.

*Cyathia*.—Quantity per corymb: About 21.Diameter of cyathia cluster: About 3.3 cm. Height, individual cyathium: About 6.5 mm. Diameter, individual cyathium: About 4.6 mm. Shape, individual cyathium: Globose. Color: Distally, close to 144B, and proximally, close to 144C. Nectaries: Quantity per cyathium: One. Size: About 2.1 mm by 3.7 mm. Texture: Smooth, glabrous. Color: Close to 2A.

*Peduncles*.—Length: About 1.8 mm. Diameter: About 1.9 mm. Texture, upper and lower surfaces: Smooth, glabrous. Aspect: Mostly upright. Color, upper and lower surfaces: Close to 144C.

*Reproductive organs*.—Stamens: Quantity per cyathia: About one to three. Filament length: About 1.9 mm. Filament color: Close to 63B. Anther length: About 0.7 mm. Anther shape: Linear and globose at apex. Anther color: Close to 59A. Pollen amount: None observed. Pistils: To date, pistil development has not been observed on plants of the new *Euphorbia*.

*Seeds and fruits*.—To date, seed and fruit development have not been observed on plants of the new *Euphorbia*.

Pathogen & pest resistance: To date, plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'BONPRI 16P5' as herein illustrated and described.

* * * * *